United States Patent [19]

Tamm

[11] 4,248,242
[45] Feb. 3, 1981

[54] OCCLUSIVE SPHYGMOMANOMETER FOR THE MEASURING OF THE ARTERIAL BLOOD PRESSURE

[76] Inventor: Ulf, S. H. Tamm, 122, chemin de la Montagne, 1224 Chene-Bougeries, Geneva, Switzerland

[21] Appl. No.: 4,725

[22] Filed: Jan. 19, 1979

[30] Foreign Application Priority Data

Jan. 20, 1978 [CH] Switzerland .................. 436788/78

[51] Int. Cl.³ .............................................. A61B 5/02
[52] U.S. Cl. .................................... 128/678; 128/680; 128/685
[58] Field of Search ................ 128/680, 681, 685, 678

[56] References Cited

U.S. PATENT DOCUMENTS

| | | | |
|---|---|---|---|
| 2,811,964 | 11/1957 | Boucke | 128/685 X |
| 3,828,811 | 8/1974 | Natkanski | 128/685 X |
| 4,112,272 | 9/1978 | Jonsson et al. | 128/675 X |
| 4,112,929 | 9/1978 | Affeldt et al. | 128/680 |
| 4,116,217 | 9/1978 | Speidel | 128/685 X |

*Primary Examiner*—Kyle L. Howell
*Attorney, Agent, or Firm*—Silverman, Cass & Singer, Ltd.

[57] ABSTRACT

An occlusive sphygomomanometer provides a single control button which allows a simultaneous modification of the rate of evacuation of air admitted into an air chamber for occlusion of an artery and the switching on and off of power to an electronic circuit treating information coming from a sensing device sensing Korotkoff noises in the artery.

6 Claims, 7 Drawing Figures

OCCLUSIVE SPHYGMOMANOMETER FOR THE MEASURING OF THE ARTERIAL BLOOD PRESSURE

BACKGROUND OF THE INVENTION

The present invention relates to an occlusive sphygmomanometer for measuring the arterial blood pressure. The device comprises an elastic air chamber intended to exert a pressure on an artery of a patient, so as to interrupt momentarily the blood circulation in the artery; a pumping device allowing the introduction of air into the air chamber; a manometer indicating the pressure in the chamber; a sensing device for the Korotkoff noises in the artery; a display device of the presence indicating the Korotkoff noises; and an electronic circuit controlling the sensing device and display device.

Such sphygmomanometers are known per se. They have the advantage of being easier to operate than conventional medical sphygmomanometers used with a stethoscope and allow patients to by themselves check their arterial blood pressure.

The purpose of the present invention is to simplify the operation of such sphygmomanometers so that the patients can use them with a minimum of training.

SUMMARY OF THE INVENTION

To this effect, the sphygmomanometer according to the invention comprises a control device ensuring the connection between the pumping device and the air chamber, and the evacuation of this chamber at two or more different rates of speed, and, simultaneously, the switching on and the switching off of the said electronic circuit. This control device comprises a manifold valve of which a manually operated movable element is integral with the means for switching on and off the electronic circuit of the sphygmomanometer.

BRIEF DESCRIPTION OF THE DRAWING

The drawings show, by way of example, one possible variety of the invention.

DESCRIPTION OF THE PREFERRED EMBODIMENT

Figure 1:
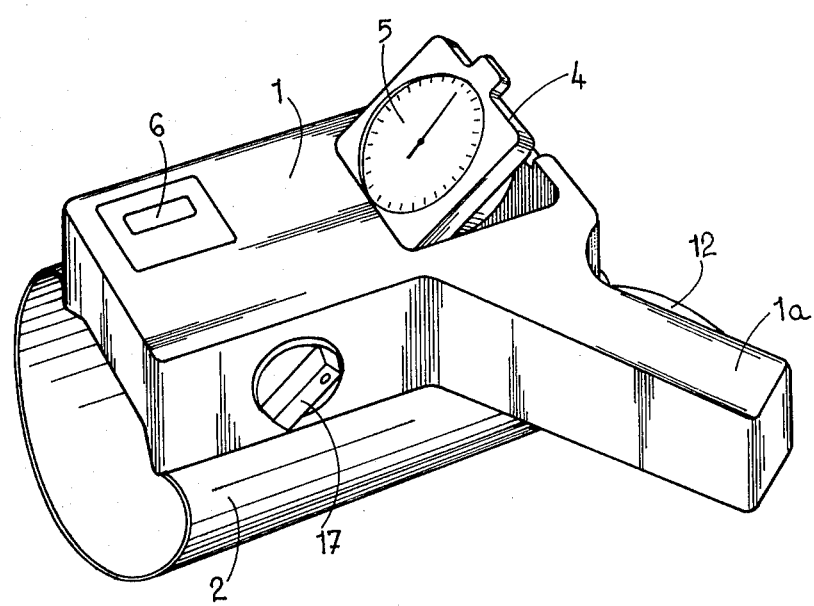
FIG. 1 is a diagrammatic perspective view of an occlusive sphygmomanometer.

The sphygmomanometer represented comprises a housing 1 having a parallelepiped general shape, provided with a flexible cuff 2 intended to be engaged on the arm of a patient. This cuff comprises in its interior an elastic air chamber diagrammatically represented at 3 in FIG. 3.

The housing 1 is provided with an articulated flap 4 carrying a manometer 5 connected, by a suitable connection, to the air chamber 3 in order to indicate the pressure within this chamber.

The cuff 2 comprises a sensor device intended to pick up Korotkoff noises, i.e. noises produced in the arterial wall during the systolic phase of the patients' heart beat.

Figure 2:
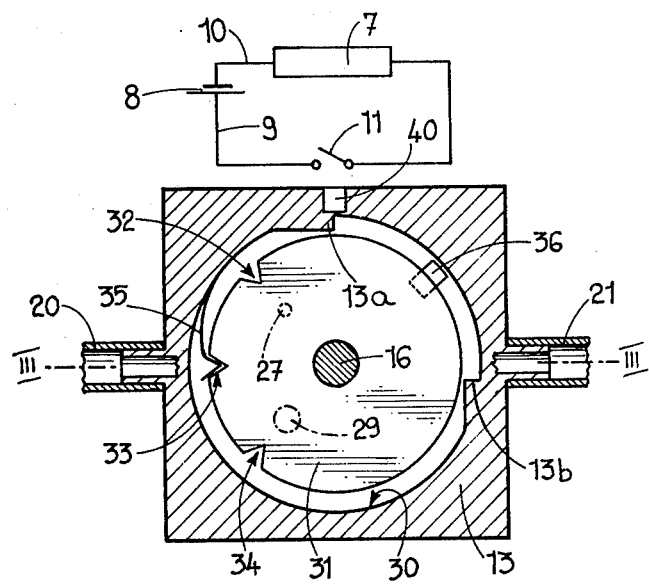
FIG. 2 is a plan sectional view of a detail, diagrammatically represented, along line II—II of FIG. 3.

The apparatus comprises moreover a display device constituted by a lamp 6 indicating the presence or the absence of the said Korotkoff noises by lighting up or not, and an electronic circuit, represented by a block 7 of FIG. 2, which is intended to amplify the signals received by the sensor device and to control the display device 6. This electronic circuit is powered by a source of current 8 the terminals of which are connected with the terminals of the circuit by a lead 9-10 comprising a magnetic reed switch 11.

Figure 3:
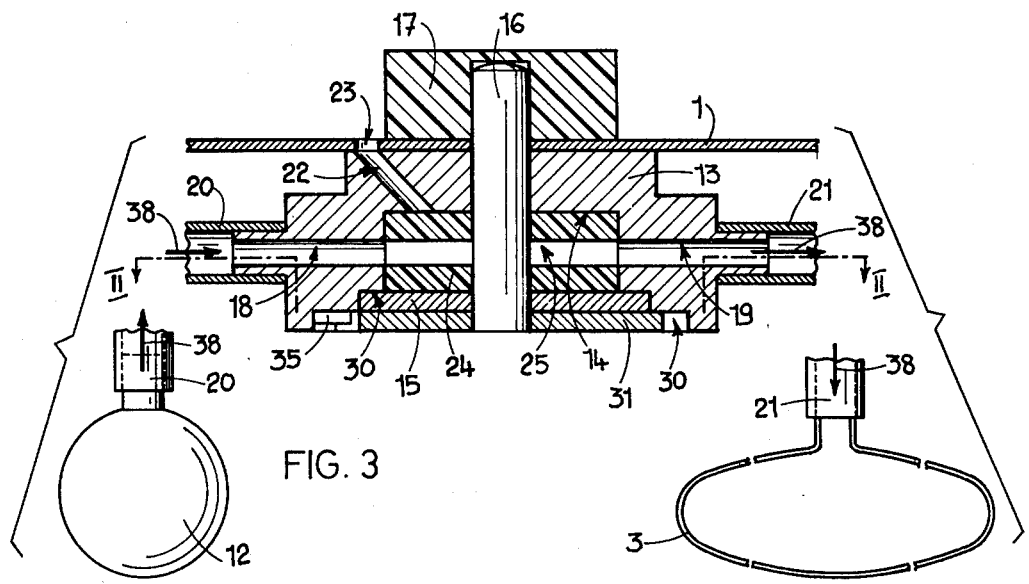
FIG. 3 is a sectional view along line III—III of FIG. 2.

The apparatus as disclosed and represented comprises moreover a hand pump 12, diagrammatically represented in FIG. 3, consisting of a rubber bulb located in a hollow protruding handle 1a of the housing 1. This rubber bulb can be operated manually.

Such an apparatus is known per se, and has not been disclosed and represented in detail.

The pump 12 is connected to the air chamber 3 by the intermediary of a control device represented in detail in FIGS. 2 to 7. This control device comprises a manifold valve including a hollow casing 13 the inner chamber of which, designated by 14, is tightly closed by a cover 15 and which is traversed by a rotative shaft 16 having a fixed control button 17 thereon which is operable manually. This casing 13 is provided with input and output passages 18 and 19, opening into the chamber 14 and aligned with each other. The input passage 18 is connected by a pipe 20 with the pumping device 12, and the output passage 19 is connected by a pipe 21, with the air chamber 3. The casing 13 is moreover provided with an exit passage 22, also opening into the chamber 14, situated opposite a hole 23 provided in the housing 1.

The shaft 16, operable by means of the control button 17 carries and fixed thereupon, a circular cylindrical body or rotary element 24 tightly located in the chamber 14. This body 24 is provided with a diametrical passage 25 (FIG. 3), with a first recessed passage 26 (FIG. 5) communicating with a passage 27 of an exactly calibrated small diameter and parallel to the axis of the body 24, and with a second recessed passage 28 (FIG. 7) communicating with a large passage 29 parallel to the calibrated passage 27. It is to be noted that the passages 27 and 29 have been represented in FIGS. 2, 4 and 6, but in dot and dash lines since the body 24 does not appear in these drawings.

At last, the shaft 16 carries, situated outside the cover 15 closing the chamber 14, and located in a recess 30 provided in the casing 13, a disc 31 provided with three notches 32, 33 and 34 fitting into a jumping spring 35 secured to the lateral wall of the recess 30 so as to ensure the stability of the several working positions of the body 24. The disc 31 carries moreover a permanent magnet 36 playing a double role. In one roll to magnet 36 serves as an abutting member preventing the control button 17 from being rotated beyond its two extreme positions, in the extreme positions the magnet 36 abuts against either an inner protrusion 13a or against an inner protrusion 13b, of the lateral wall of the recess 30. In the other role magnet 36 serves to control, in a working position of the control device, the switch 11.

Figure 4:
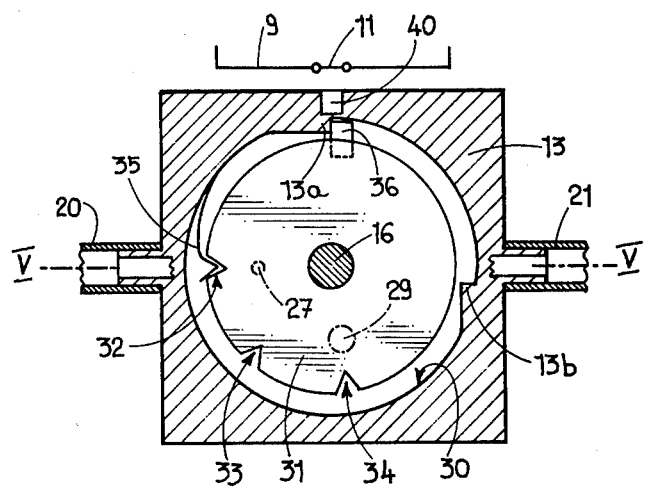
FIG. 4 is a plan sectional view of the same detail, but represented in another working position, along line IV—IV of FIG. 5.
Figure 5:
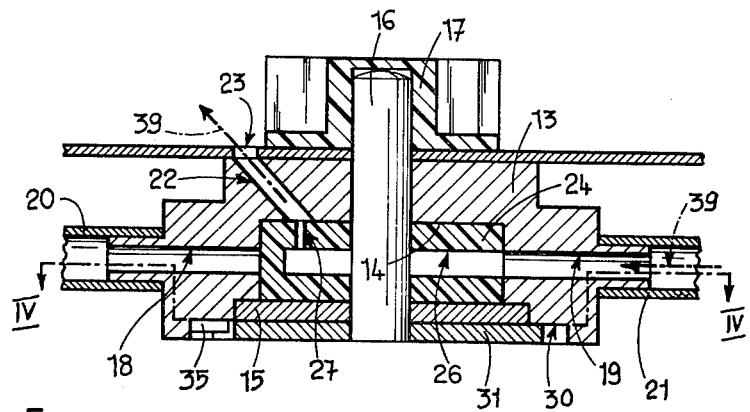
FIG. 5 is a sectional view along line V—V of FIG. 4.

The patient engages the cuff 2 on his or her arm with the cuff maintaining itself elastically on the patient's arm. The patient then brings the control button 17 into a first position, marked on the housing by indications not represented in the drawing, corresponding to the position shown in FIGS. 2 and 3, in which the diametrical passage 25 of the body 24 is aligned with the passages 18 and 19 of the casing 13. However, the passage 22 of the casing 13 is closed by the body 24. In this position of the control device, the operation of the pump 12 allows inflation of the air chamber 3, as indicated by the several arrows 38 of FIG. 3. When a certain pressure is reached, as indicated by the manometer 5, at which the circulation of the blood in the artery on which the apparatus acts is certain to be interrupted, the button 17 is brought into a second working position (FIGS. 4 and 5). In the second working position, the recessed passage 26 of the body 24 is situated opposite the passage 19 and its calibrated passage 27 is situated opposite the passage 22. In this position of the control device, the air chamber 3 evacuates slowly, as indicated by the arrows 39 of FIG. 5, the air being able to pass through the passage 27 only at a very slow rate of speed. In the second working position of the control device, the permanent magnet 36 is situated in the vicinity of and controls the closing of the magnetic reed switch 11. A small bar of soft iron 40 is located in the casing 13 opposite the abutment 13a, so as to conduct the magnetic field of the magnet 36 in the direction of the switch 11.

When the switch 11 is closed, the electronic circuit 7 is powered by the source of current 8 and enters into operation. It produces the lighting of the lamp 6 as soon as the Korotkoff noises are perceptible in the compressed artery, i.e. when the blood circulation starts again. The patient then reads the corresponding pressure on the manometer 5. When the artery is entirely released, the Korotkoff noises are no longer perceptible by the sensor so that the lamp 6 is switched off at this time. The patient also then reads the corresponding pressure on the manometer 5.

Figure 6:
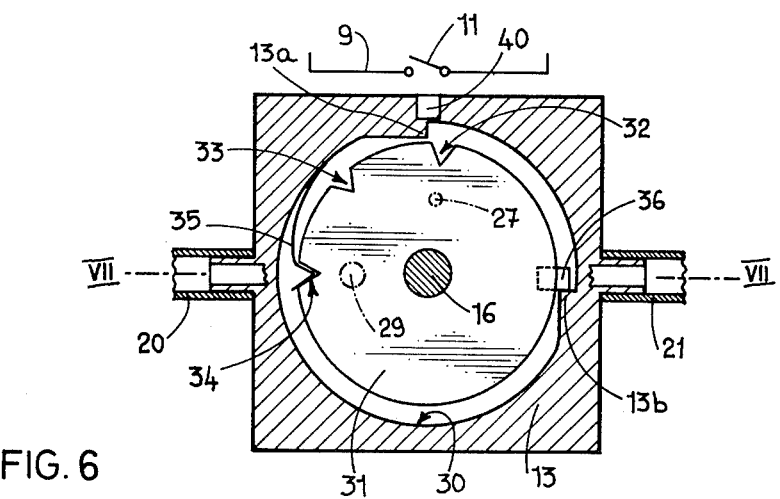
FIG. 6 is a plan sectional view of the same detail, but represented in a third working position, along line VI—VI of FIG. 7.
Figure 7:
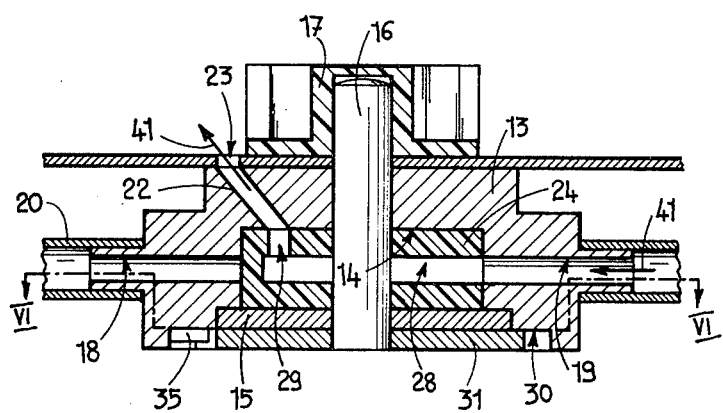
FIG. 7 is a sectional view along line VII—VII of FIG. 6.

When the readings are ended, the patient brings the control device into its third position, represented in FIGS. 6 and 7, in which the recessed passage 28 of the body 24 is situated opposite the passage 19 of the casing 13 and the passage 29, of large section cross, is situated opposite the passage 22. The passage 29 being of a much greater diameter than the calibrated passage 27, the air chamber 3 is rapidly deflated, as indicated by the arrows 41 of FIG. 7. Moreover, in this position, the magnet 36 is no longer situated opposite the switch 11 so that switch 11 is opened and the electronic circuit 7 is no longer powered.

What I claim is:

1. An occlusive sphygmomanometer for measuring an arterial blood pressure, comprising:
   an elastic air chamber which is engageable around the arm of a patient to exert a pressure on an artery of the patient's arm when inflated and thereby momentarily interrupt the blood circulation in the artery;
   a pumping device connectable to the air chamber to inflate the air chamber by introducing air thereinto;
   a manometer connected to the air chamber and indicating the air pressure in the chamber;
   sensor means fixed on the air chamber for sensing the Korotkoff noises produced in an artery during the systolic phase of a heart beat and having an output producing a signal in response thereto;
   a display device coupled to the sensor means to display the presence of Korotkoff noises sensed by the sensor means;
   an electronic circuit coupling the sensor means output signal to the display device to amplify the signal and control the display device; and
   a control device comprising a rotary manifold valve having a manually operable rotary element, and switching means for switching on and off power to the electronic circuit integral with the rotary element, the rotary manifold valve connecting the air pump to the air chamber through the rotary element when the element is in a first rotary position, the rotary manifold valve connecting the air chamber through the rotary element to the exterior of the valve when the element is in a second rotary position to provide evacuation of air from the chamber at a slow rate of speed and the rotary manifold valve connecting the air chamber to the exterior of the valve through the rotary element when the element is in a third rotary position to provide evacuation of air from the chamber at a fast rate of speed greater than the slow rate of speed, and the switching means respectively switching on and off power to the electronic circuit when the element is rotated to and from the second position.

2. The sphygmomanometer as claimed in claim 1 in which the electronic circuit includes a magnetic reed switch connected in series with the power supply of the circuit and located adjacent the switching means when the rotary element is in the second position, and the switching means include a magnet so that when the magnet is adjacent the magnetic reed switch, the reed switch is closed connecting power to the electronic circuit.

3. The sphygmomanometer as claimed in claim 1 in which the rotary manifold valve includes a casing having a chamber interior thereof, and having an input passage connected to the pumping device, an output passage connected to the air chamber and an exit passage open to the exterior of the casing, the input, output and exit passages opening into the chamber and the rotary element being a cylindrical body rotatively mounted in the chamber and having passages therein for interconnecting said input, output and exit passages.

4. The sphygmomanometer as claimed in claim 3 in which said rotary element includes a first passage therethrough connecting the input passage to the output passage when in the first rotary position to provide connection of the pumping device to the air chamber.

5. The sphygmomanometer as claimed in claim 4 in which said rotary element includes a second passage therethrough having a small diameter for at least a portion thereof, said second passage connecting the output passage to the exit passage when the element is in the second rotary position to provide the evacuation of air from the chamber at the slow rate of speed.

6. The sphygmomanometer as claimed in claim 5 in which said rotary element includes a third passage therethrough having a large diameter greater than said small diameter for at least a portion thereof, said third passage connecting the output passage to the exit passage when the element is in the third rotary position to provide the evacuation of air from the chamber at the fast rate of speed greater than the slow rate of speed.

* * * * *

UNITED STATES PATENT AND TRADEMARK OFFICE
CERTIFICATE OF CORRECTION

PATENT NO. : 4,248,242
DATED : February 3, 1981
INVENTOR(S) : Ulf S. H. Tamm

It is certified that error appears in the above—identified patent and that said Letters Patent are hereby corrected as shown below:

On the Title page, item [30], change "436788/78" to --436/78-8--.

*Signed and Sealed this*

*Twenty-sixth* Day of *May 1981*

[SEAL]

*Attest:*

RENE D. TEGTMEYER

*Attesting Officer*    *Acting Commissioner of Patents and Trademarks*